US010001456B2

(12) United States Patent
Campbell et al.

(10) Patent No.: US 10,001,456 B2
(45) Date of Patent: Jun. 19, 2018

(54) METHODS FOR DETECTION IN DIFFERENTIAL MOBILITY SPECTROMETER USING A PEPTIDE METAL COMPLEX

(71) Applicant: DH Technologies Development PTE Ltd., Singapore (SG)

(72) Inventors: John L Campbell, Milton (CA); Yves LeBlanc, Newmarket (CA); Chang Liu, Richmond Hill (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days. days.

(21) Appl. No.: 15/511,712

(22) PCT Filed: Aug. 28, 2015

(86) PCT No.: PCT/IB2015/056534
§ 371 (c)(1),
(2) Date: Mar. 16, 2017

(87) PCT Pub. No.: WO2016/030860
PCT Pub. Date: Mar. 3, 2016

(65) Prior Publication Data
US 2017/0248547 A1    Aug. 31, 2017

Related U.S. Application Data

(60) Provisional application No. 62/044,171, filed on Aug. 29, 2014.

(51) Int. Cl.
*C07K 1/14*    (2006.01)
*C07K 1/00*    (2006.01)
(Continued)

(52) U.S. Cl.
CPC ............ *G01N 27/624* (2013.01); *H01J 49/04* (2013.01); *H01J 49/10* (2013.01)

(58) Field of Classification Search
USPC .... 250/281, 282, 288, 526; 435/5, 6.1, 6.11, 435/6.5, 6.16, 6.18, 6.19, 89, 87, 90,
(Continued)

(56) References Cited

U.S. PATENT DOCUMENTS 7,955,810 B2 *   6/2011   Agus .................. G01N 33/6803
                                                                422/50
7,968,842 B2 *   6/2011   Zapata ................ H01J 49/0404
                                                                250/288
(Continued)

FOREIGN PATENT DOCUMENTS

WO      02/074927 A2      9/2002
WO      2008148645 A1    12/2008
WO      2014102577 A1     7/2014

OTHER PUBLICATIONS

International Search Report and Written Opinion for PCT/IB2015/056534 dated Dec. 17, 2015.
(Continued)

*Primary Examiner* — Bernard Souw

(57) ABSTRACT

Methods and systems for separating and/or quantifying peptides using differential mobility spectrometry (DMS) are provided herein. In accordance with various aspects of the applicant's teachings, the methods and systems can provide for the separation of one or more peptides, for example, peptides that may be difficult to separate with conventional techniques, such as mass spectrometry (MS), by complexing the peptides with a metal cation (e.g., Ca2+) prior to DMS. In some aspects, the present teachings can prevent proton stripping from ionized peptides that can occur in DMS to
(Continued)

prevent unintended and/or undesirable alterations to the peptide's charge state distribution.

19 Claims, 7 Drawing Sheets

(51) Int. Cl.
| | |
|---|---|
| *B01D 59/44* | (2006.01) |
| *B01D 15/38* | (2006.01) |
| *B01D 15/36* | (2006.01) |
| *C12Q 1/68* | (2018.01) |
| *G01N 33/53* | (2006.01) |
| *H01J 49/26* | (2006.01) |
| *G01N 27/62* | (2006.01) |
| *H01J 49/04* | (2006.01) |
| *H01J 49/10* | (2006.01) |

(58) Field of Classification Search
USPC .......... 435/91.1; 436/50, 52, 86, 183, 529; 530/412, 416, 300, 304, 305, 333, 810
See application file for complete search history.

(56) References Cited

U.S. PATENT DOCUMENTS

| | | | | |
|---|---|---|---|---|
| 8,217,338 B2* | 7/2012 | Krueger | ............... | G01N 27/622 250/281 |
| 8,242,442 B2* | 8/2012 | Krueger | ............... | G01N 27/622 250/281 |
| 8,492,709 B2* | 7/2013 | Krueger | ............... | G01N 27/622 250/281 |
| 8,618,477 B2* | 12/2013 | Krueger | ............... | G01N 27/622 250/281 |
| 9,177,774 B2* | 11/2015 | Brunelli | ............... | G01N 27/624 |
| 2002/0113207 A1 | 8/2002 | Lee | | |
| 2009/0078865 A1* | 3/2009 | Zapata | ................ | G01N 27/624 250/288 |
| 2010/0055697 A1* | 3/2010 | Agus | ................ | G01N 33/6803 435/6.13 |
| 2010/0127166 A1* | 5/2010 | Krueger | ............... | G01N 27/622 250/282 |
| 2010/0148058 A1* | 6/2010 | Krueger | ............... | G01N 27/622 250/282 |
| 2011/0174964 A1* | 7/2011 | Brunelli | ............... | G01N 27/624 250/282 |
| 2012/0261567 A1* | 10/2012 | Voorhees | ............ | H01J 49/0418 250/282 |
| 2012/0273667 A1* | 11/2012 | Krueger | ............... | G01N 27/622 250/252.1 |
| 2012/0285831 A1 | 11/2012 | Caulfield et al. | | |
| 2012/0305761 A1* | 12/2012 | Krueger | ............... | G01N 27/622 250/282 |

OTHER PUBLICATIONS

Wyttenbach T et al. "Interactions of the hormone oxytocin with divalent metal icons", Journal of the American Chemical Society, American Chemical Society, US, vol. 130, Jan. 10, 2008 pp. 5993-6000 and supporting information on pp. S1-S36 of Journal of the American Chemical Society, May 7, 2008.

* cited by examiner

Note: [M+2H]2+ is not observed when MeOH or IPA are used as modifier in the DMS

US 10,001,456 B2

METHODS FOR DETECTION IN DIFFERENTIAL MOBILITY SPECTROMETER USING A PEPTIDE METAL COMPLEX

RELATED APPLICATIONS

The present application claims the benefit of priority from U.S. Provisional Application Ser. No. 62/044,171, filed on Aug. 29, 2014, the entire contents of which are hereby incorporated by reference.

FIELD

The present teachings generally relate to mass spectrometry, and more particularly to methods and apparatus for the separation and/or quantitation of peptides using differential mobility spectrometry.

BACKGROUND

Mass spectrometric detection/quantitation of peptides has traditionally required the precise selection of unique MRM transitions. However, in many instances, peptides may not fragment with high efficiency (especially cyclic peptides such as oxytocin), which can lead to additional sensitivity losses (e.g., during the MS/MS stage). Also, peptides can be difficult to quantitate when present in a crude sample (e.g., a biological sample) or a mixture containing other peptides, biological molecules, chemicals, proteins, lipids, etc. Though additional emphasis has been placed on improving sample preparation techniques (e.g., immunocapture, nanoLC, microLC), such techniques can increase cost, complexity, and/or throughput of the analysis, for example, due to the care required in column loading, equilibration time, and optimizing the flow rate.

Previous attempts at detection of peptides using differential mobility spectrometry have shown promise, however, as peptides can exhibit unique behaviors within a differential mobility spectrometer (DMS). For example, some peptides have the tendency to separate from singly charged chemical noise and separate based on the peptide's charge states. It has also been shown, however, that use of a chemical modifier in the transport region of a DMS can lead to alterations of the detected peptide states through proton stripping from the peptide and ultimately hinder detection of the peptide as a multiply charged ion. Accordingly, there remains a need for improved quantitation of peptides with enhanced discrimination between charged species.

SUMMARY

Described herein are methods and systems for detection of peptides using differential mobility spectrometry (DMS). In accordance with various aspects of the present teachings, the methods comprise forming a peptide metal complex and transporting the complex through a DMS to separate, detect, and/or quantify the peptide. The resolution of the ion signals can in turn allow for accurate quantification of such peptides in a sample containing them.

In accordance with one aspect, certain embodiments of the applicant's teachings relate to a method for separating one or more peptides in a sample. The method comprises combining the sample comprising (or suspected of comprising) one or more peptides with a solution comprising a metal so as to form one or more peptide metal complexes, ionizing said one or more peptide metal complexes so as to form one or more peptide metal ion complexes, and transporting said one or more peptide metal ion complexes through a differential mobility spectrometer to effect separation of said one or more peptide metal ion complexes.

In another aspect, the present teachings provide a method for analyzing a sample containing or suspected of containing one or more peptides. The method comprises forming one or more peptide metal complexes from said one or more peptides, ionizing said one or more peptide metal complexes so as to form one or more peptide metal ion complexes, and transporting said one or more peptide metal ion complexes through a differential mobility spectrometer (e.g., a High-Field Asymmetric Waveform Ion Mobility Spectrometry (FAIMS)) to effect separation of said one or more peptide metal ion complexes.

In yet another aspect, the present teachings provide a method for quantifying one or more peptides. The method comprises ionizing a sample containing one or more peptide metal complexes so as to form one or more peptide metal ion complexes, transporting the one or more peptide metal ion complexes through a differential mobility spectrometer to effect separation of said one or more peptide metal ion complexes, and quantifying said one or more peptides.

In another aspect, the present teachings provide a method for separating one or more peptides. The method comprises transporting one or more peptide metal ion complexes through a differential mobility spectrometer to effect separation of said one or more peptide metal ion complexes.

In one aspect, the present teachings provide a method of separating one or more peptides in a sample. The method comprises combining the sample comprising one or more peptides with a solution comprising a calcium salt, so as to form one or more peptide calcium complexes, ionizing said one or more peptide calcium complexes so as to form one or more peptide calcium ion complexes, and transporting said mixture through a differential mobility spectrometer to effect separation of said one or more peptide calcium ion complexes. In some aspects, DMSO can also be added to the mixture of the sample and calcium salt In one embodiment of the methods described herein, the metal comprises a metal cation. In some embodiments, the metal cation is obtained from the group comprising alkali metals, alkaline earth metals, transition metals, and salts thereof. In some embodiments, the metal comprises a salt of said metal. By way of example, in one embodiment, the metal or metal cation can comprise calcium, which can optionally be in the form of a calcium salt. For example, the calcium salt can be one of calcium chloride ($CaCl_2$) or calcium carbonate ($CaCO_3$).

In accordance with the present teachings, the one or more peptides can be selected from the group consisting of polypeptides, oligopeptides, proteins, neuropeptides, lipopeptides, cyclic peptides, lasso peptides, and peptide hormones. In other embodiments, the one or more peptides can be selected from the group consisting of tachykinin peptides, vasoactive intestinal peptides, pancreatic polypeptide-related peptides, opioid peptides, and calcitonin peptides. For example, the peptide can be oxytocin. In another embodiment, the one or peptides comprises at least two amino acids.

The methods described herein can further comprise adding a chemical modifier to the peptide metal ion complexes during said transporting step. For example, any chemical modifier known in the art and modified in accordance with the present teachings could be used such as any volatile liquid (e.g., phenols, propanol, ethanol, acetone, DMF, THF, benzene), including alcohols, alkanes, alkenes, halogenated alkanes and alkenes, furans, esters, ethers, and aromatic compounds, all by way of non-limiting example. In one aspect, the chemical modifier can be selected from the group consisting of methanol, isopropanol, acetonitrile and dimethyl sulfoxide (DMSO).

In various aspects, the methods described herein can further comprise detecting and/or determining the abundance of the one or more peptides in the sample.

In some aspects, the methods described herein can further comprise modulating a throttle gas flow rate to modulate a drift time of the one or more peptide metal ion complexes in the differential mobility spectrometer.

In various aspects, the sample is not passed through a liquid chromatography column prior to being transmitted through the differential mobility spectrometer.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

Methods and systems for separating and/or quantifying peptides using differential mobility spectrometry (DMS) are provided herein. In accordance with various aspects of the applicant's teachings, the methods and systems can provide for the separation of one or more peptides, for example, peptides that may be difficult to separate with conventional techniques, such as mass spectrometry (MS), by complexing the peptides with a metal cation (e.g., mixing the sample with a solution containing the metal cation prior to transporting a peptide metal ion complexes through the DMS). In various aspects, methods and systems in accordance with applicant's teachings can enable a differential mobility spectrometer to resolve one or more peptides in a sample. In some aspects, the present teachings can prevent proton stripping from ionized peptides that can occur in DMS to prevent unintended and/or undesirable alterations to the peptide's charge state distribution.

Figure 1:
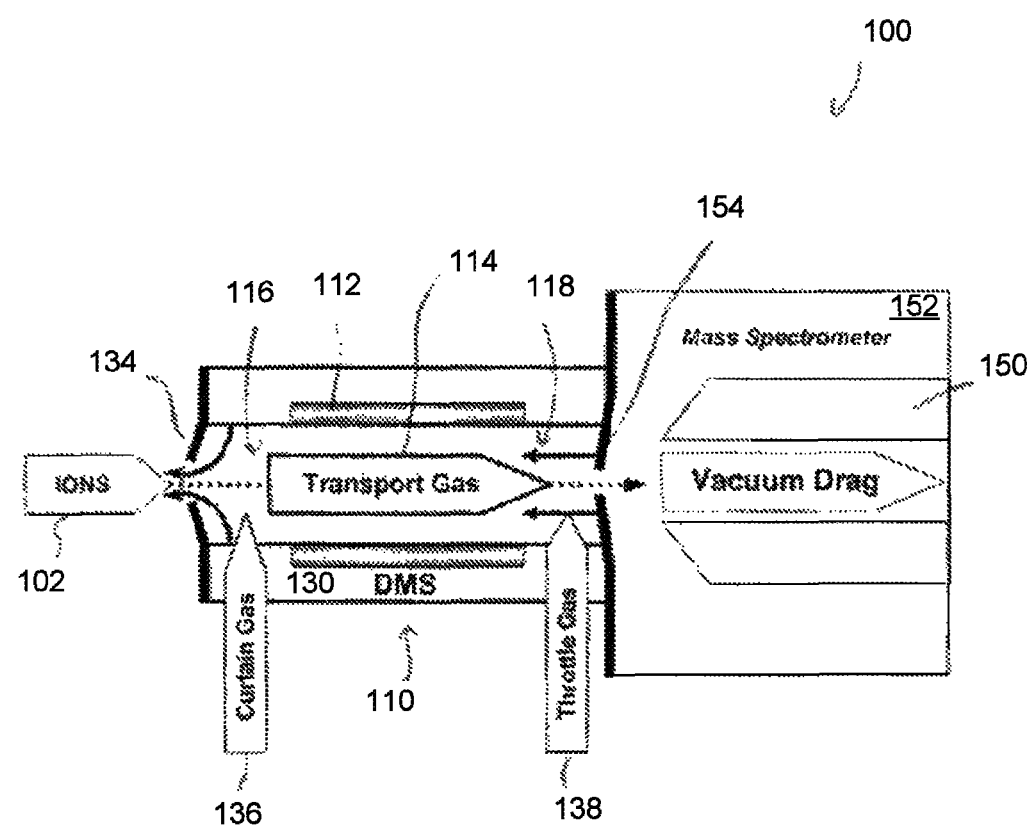
FIG. 1, in a schematic diagram, illustrates an exemplary differential mobility spectrometer/mass spectrometer system including a curtain gas supply and a throttle gas supply in accordance with an aspect of various embodiments of the applicant's teachings.

Referring now to FIG. 1, an exemplary differential mobility spectrometer/mass spectrometer system 100 in accordance with various aspects of applicant's teachings is illustrated schematically. As shown in FIG. 1, the differential mobility spectrometer/mass spectrometer system 100 generally comprises a differential mobility spectrometer 110 in fluid communication with a mass spectrometer (hereinafter generally designated mass spectrometer 150). As will be appreciated by a person skilled in the art, the differential mobility spectrometer/mass spectrometer system 100 represents only one possible configuration for use in accordance with various aspects of the systems, devices, and methods described herein.

The differential mobility spectrometer 110 can have a variety of configurations, but is generally configured to resolve ions 102 (e.g., peptide metal ion complexes) based on their mobility through a fixed or variable electric field (whereas MS analyzes ions based on their mass-to-charge ratios). For example, the differential mobility spectrometer 110 can be a differential mobility spectrometer (DMS), or a high-field asymmetric waveform ion mobility spectrometer (FAIMS) of various geometries such as parallel plate (eg. SelexION™ Technology sold by SCIEX), curved electrode, or cylindrical FAIMS device, among others. In DMS, RF voltages, often referred to as separation voltages (SV), can be applied across the drift tube in a direction perpendicular to that of a drift gas flow. Ions of a given species tend to migrate radially away from the axis of the transport chamber by a characteristic amount during each cycle of the RF waveform due to differences in mobility during the high field and low field portions. A DC potential, commonly referred to as a compensation voltage (CV or CoV), applied to the drift tube provides a counterbalancing electrostatic force to that of the SV. The CV can be tuned so as to preferentially prevent the drift of a species of the ion(s) of interest. Depending on the application, the CV can be set to a fixed value to pass only an ion species with a particular differential mobility while the remaining species of ions drift toward the electrodes and are neutralized. Alternatively, if the CV is scanned for a fixed SV as a sample is introduced continuously into the device, a mobility spectrum can be produced as the device transmits ions of different differential mobilities. For greater certainty, when referring to a differential mobility spectrometer, it should be appreciated that included within the scope of this term are all devices which operate to separate ions based on their mobility properties, including a drift-time ion mobility spectrometer, a traveling wave ion mobility spectrometer, or other similar technology.

In the exemplary embodiment depicted in FIG. 1, the differential mobility spectrometer 110 is contained within a curtain chamber 130 that is defined by a curtain plate or boundary member 134 and is supplied with a curtain gas 136 from a curtain gas supply (not shown). As shown, the exemplary differential mobility spectrometer 110 comprises a pair of opposed electrode plates 112 that surround a transport gas 114 that drifts from an inlet 116 of the differential mobility spectrometer 110 to an outlet 118 of the differential mobility spectrometer 110. The outlet 118 of the differential mobility spectrometer 110 releases the drift gas 116 into an inlet 154 of a vacuum chamber 152 containing the mass spectrometer 150. A throttle gas 138 can additionally be supplied at the outlet 118 of the differential mobility spectrometer 110 so as to modify the flow rate of transport gas 114 through the differential mobility spectrometer 110.

In accordance with certain aspect of the present teachings, the curtain gas 136 and throttle gas 114 can be set to flow rates determined by a flow controller and valves so as to alter the drift time of ions within the differential mobility spectrometer 110. Each of the curtain and throttle gas supplies can provide the same or different pure or mixed composition gas to the curtain gas chamber. By way of non-limiting example, the curtain gas can be air, $O_2$, He, $N_2$, $CO_2$, or any combinations thereof. Additionally, the system 110 can also include a modifier supply (not shown) for supplying a modifier and/or reagent to the curtain and throttle gases. The pressure of the curtain chamber 130 can be maintained, for example, at or near atmospheric pressure (i.e., 760 Torr).

One or more chemical modifiers can be added in the transport region of the differential mobility spectrometer 110. The chemical modifier, for example, can be independently added to the transport region or added along with the curtain gas 136. By way of non-limiting example, the chemical modifier can be methanol, isopropanol, acetonitrile, or dimethyl sulfoxide (DMSO).

Figure 4:
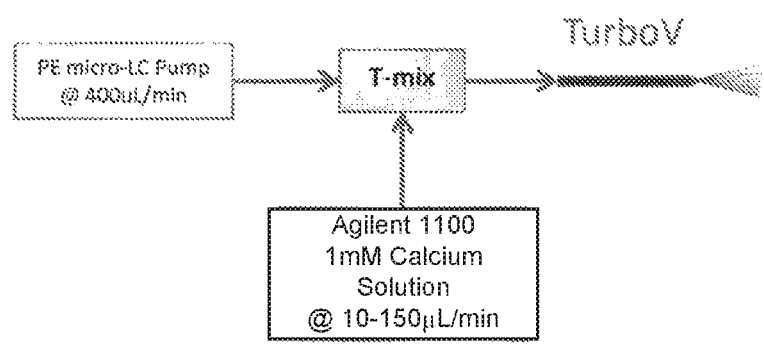
FIG. 4 illustrates a schematic diagram of an exemplary high performance liquid chromatography (HPLC) system including a liquid chromatography pump and ion source in accordance with aspects of various embodiments of the applicant's teachings.

Ions 102 (e.g., peptide metal ion complex) can be provided from an ion source (e.g., as shown in FIG. 4) and emitted into the curtain chamber 130 via curtain chamber inlet 150. As will be appreciated by a person skilled in the art, the ion source can be virtually any ion source known in the art, including for example, an electrospray ionization (ESI) source. The pressure of the curtain gases in the curtain chamber 130 (e.g., ~760 Torr) can provide both a curtain gas outflow out of curtain gas chamber inlet, as well as a curtain gas inflow into the differential mobility spectrometer 110, which inflow becomes the transport gas 114 that carries the ions 102 through the differential mobility spectrometer 110 and into the mass spectrometer 150 contained within the vacuum chamber 152, which can be maintained at a much lower pressure than the curtain chamber 130. By way of non-limiting example, the vacuum chamber 152 can be maintained at a pressure lower than that of the curtain chamber 130 (e.g., by a vacuum pump) so as to drag the transport gas 114 and ions 102 entrained therein into the inlet 154 of the mass spectrometer 150.

As will be appreciated by a person skilled in the art, the differential mobility/mass spectrometer system 100 can additionally include one or more additional mass analyzer elements downstream from vacuum chamber 152. Ions 102 can be transported through vacuum chamber 152 and through one or more additional differentially pumped vacuum stages containing one or more mass analyzer elements. For instance, in one embodiment, a triple quadrupole mass spectrometer may comprise three differentially pumped vacuum stages, including a first stage maintained at a pressure of approximately 2.3 Torr, a second stage maintained at a pressure of approximately 6 mTorr, and a third stage maintained at a pressure of approximately $10^{-5}$ Torr. The third vacuum stage can contain a detector, as well as two quadrupole mass analyzers with a collision cell located between them. It will be apparent to those skilled in the art that there may be a number of other ion optical elements in the system. Alternatively, a detector (e.g., a Faraday cup or other ion current measuring device) effective to detect the ions transmitted by the differential mobility spectrometer 110 can be disposed directly at the outlet of the differential mobility spectrometer 110.

In accordance with various aspects of the applicant's teachings, the exemplary system discussed above with reference to FIG. 1 can be used to analyze one or more peptides (e.g., one or more peptide metal ion complexes) contained within a sample. In accordance with certain aspects of the present teachings, one or more peptide molecules (generally designated herein as M) contained within a sample can be ionized. For example, a metal ion (generally designated as X) can be added to a peptide so as to form a peptide metal complex ($[M+X]^+$). By way of example, a peptide (e.g., oxytocin) can be complexed by associating the peptide with a metal cation (e.g. calcium, zinc, copper, and magnesium), so as to generate a peptide metal complex such as $[M+Ca]^{2+}$, respectively, all by way of non-limiting example.

In accordance with various aspects of the present teachings, applicant has discovered that by complexing one or more peptides with a metal cation so as to form one or more peptide metal complexes, differential mobility spectrometry can enable improved separation of peptide metal ion complexes relative to protonated peptides alone, while reducing charge state distribution caused by proton stripping. By way of example, peptide metal complexes, formed via exposure to a mixture of peptides to metal cations, can be sufficiently separated using differential mobility spectrometry so as to allow the independent quantitation of the peptides from which the peptide metal complexes were derived. Without being bound to any particular theory, it is believed that the association of the peptides with the metal cations can help lock the peptides into stable configurations that exhibit a resolvable, characteristic response when subjected to differential mobility spectrometry.

Accordingly, in operation, a sample containing or suspected of containing one or more peptides can be complexed with a metal cation, for example, so as to form peptide metal complex. As discussed above, the sample containing peptide metal ion complexes can be emitted into the curtain chamber 130 (e.g., from an ion source such as ESI) and transported through the differential mobility spectrometer 110 to effect separation of the peptide metal ion complex. A chemical modifier can be added to transport region of the DMS to further enhance separation of the peptide metal ion complex. According to various aspects, the differential mobility spectrometer 110 can be operated at a fixed SV with the CV scanned so as to serially pass various ions. The ions transmitted by the differential mobility spectrometer can then be sent to downstream mass analyzer elements 150 for detection and/or further analysis.

It will be appreciated in view of the present teachings that a variety of peptides within a sample can be separated or quantified with DMS including, but not limited to, polypeptides, oligopeptides, proteins, neuropeptides, lipopeptides, cyclic peptides, lasso peptides, and peptide hormones. Additional types of peptides to which the present teachings can be applied include, for example, tachykinin peptides, vasoactive intestinal peptides, pancreatic polypeptide-related peptides, opioid peptides, and calcitonin peptides, all by way of non-limiting example. For example, in an exemplary embodiment, the peptide can be oxytocin.

The peptides can be derived from a variety of samples including, for example, a biological sample. Biological samples can comprise, for example, any bodily fluid, such as an intracellular fluid, an extracellular fluid, urine, blood, CSF (cerebrospinal fluid), saliva, bile, amniotic fluid, lymph, etc. The sample can also comprise, for example, a crude sample or a purified sample.

As described herein, the methods comprise combining the one or more peptides with a metal cation so as to form a peptide metal complex. The metal cation, for example, can comprise any suitable metal found in the periodic table of elements. For example, the one or more peptides can complex with any group 2 (alkaline earth metal) element (e.g., Be, Mg, Ca, Sr, Ba, or Ra), alkali metal and transition metal. The metal cation can also be obtained from any salt of the foregoing, e.g., $CaCO_3$, $CaCl_2$, calcium acetate, calcium bicarbonate, etc. In addition, other chemical agents may be present when combining the sample or peptides with the metal cation. For example, the applicant has discovered that the addition of DMSO may provide further, unexpected benefits to that of the metal cation alone.

The methods and systems described herein further comprise adding a chemical modifier. The chemical modifier is added to one or more ionized peptide metal complex (e.g., peptide metal ion complex) in a transport region of a DMS. For example, any chemical modifier known in the art and modified in accordance with the present teachings could be used such as any volatile liquid (e.g., phenols, propanol, ethanol, acetone, DMF, THF, benzene), including alcohols, alkanes, alkenes, halogenated alkanes and alkenes, furans, esters, ethers, and aromatic compounds, all by way of non-limiting example. Adding a chemical modifier in the transport region modulates the separation behavior of the one or more peptide metal ion complexes. In certain embodiments, the chemical modifier increases the separation of the one or more peptide metal ion complex. The chemical modifier, for example, comprises methanol, isopropanol, acetonitrile or dimethyl sulfoxide (DMSO).

EXAMPLES

The applicant's teachings can be even more fully understood with reference to the following examples and data presented in FIGS. 2-6, which demonstrate the separation of peptides using differential mobility spectrometry in accordance with various aspects of the teachings herein. Other embodiments of the applicant's teachings will be apparent to those skilled in the art from consideration of the present specification and practice of the present teachings disclosed herein. It is intended that these examples be considered as exemplary only.

Figure 2:
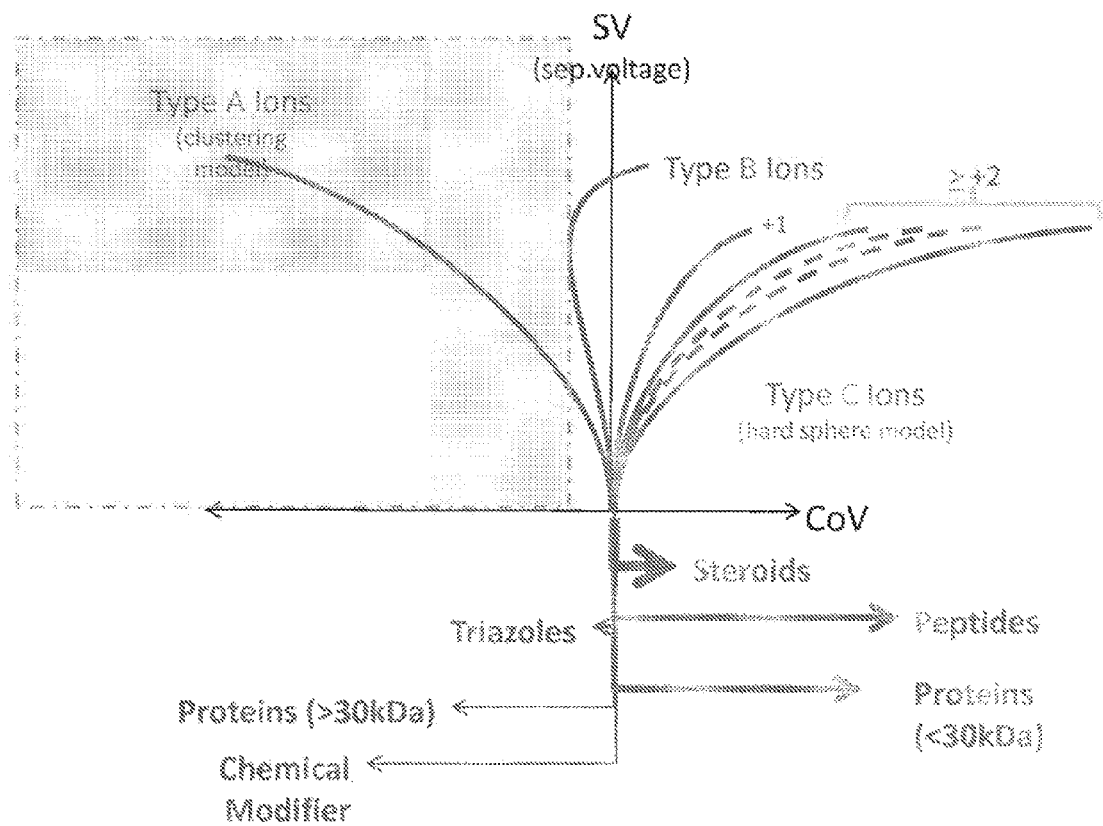
FIG. 2 depicts the various exemplary behaviors of various compounds in a differential mobility spectrometer.

Example 1—A method for Selective Detection in DMS Using a Peptide-Metal Ion Complex As noted above, peptides are known to exhibit unique behavior in DMS. Peptides can separate from singly charged chemical noise and also separate based on their different charge states. Furthermore, using chemical modifiers, for example, isopropanol (IPA), methanol, acetonitrile (AcCN), or DMSO in the transport region can change or modulate the separation behavior of peptides in the DMS. Though using a chemical modifier can significantly increase the separation capability of the DMS, a chemical modifier in the transport region of the DMS can also alter the observed peptide charge state distribution and hinder the detection of the peptide as a multiply charged ion. In some cases, a chemical modifier can hinder the detection of the peptide as a multiply charged ion, due to proton stripping from the peptide in the gas phase by the chemical modifier to alter DMS behavior (SV/CoV value), as follows, for example: $[M+2H]^{2+}+IPA\ gas \rightarrow [M+H]^{+}+[IPA+H]^{+}$ Further as shown in FIG. 2, the added chemical modifier can interact with a peptide functional group (predominantly around the charge site) and alter its DMS behavior. In many cases, the peptide can be changed from a C-type to either an A-type or B-type, depending on the interaction strength.

A separation of an exemplary peptide using DMS will now be described with reference to oxytocin (OT), which has the following structure:

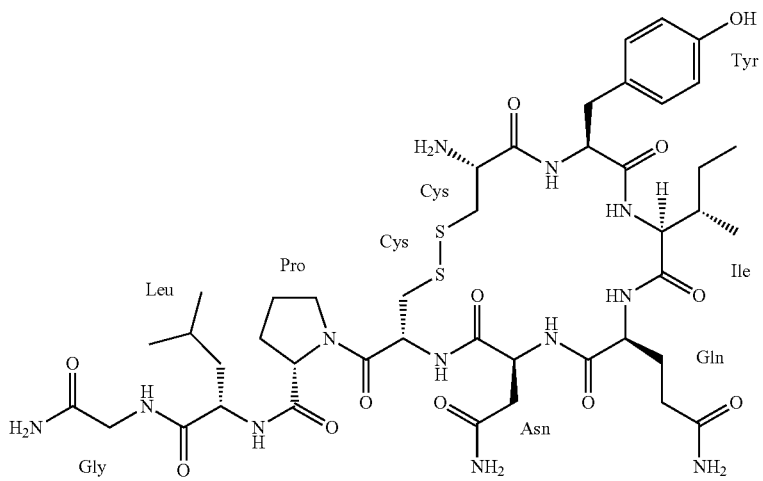 [SMILES: CC[C@H](C)[C@@H]1NC(=O)[C@H](Cc2ccc(O)cc2)NC(=O)[C@@H](N)CSSC[C@@H](C(=O)N2CCC[C@H]2C(=O)N[C@@H](CC(C)C)C(=O)NCC(N)=O)NC(=O)[C@H](CC(N)=O)NC(=O)[C@H](CCC(N)=O)NC1=O]

Figure 3A:
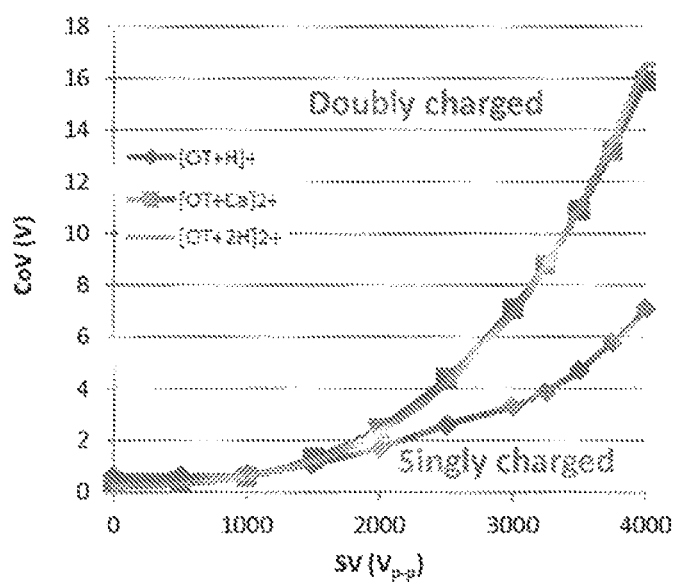
FIG. 3A-3D depict exemplary data for a protonated and calciated peptide (oxytocin) as transmitted by a differential mobility spectrometer in the presence of various modifiers and subsequently detected in accordance with aspects of various embodiments of the applicant's teachings.
Figure 3B:
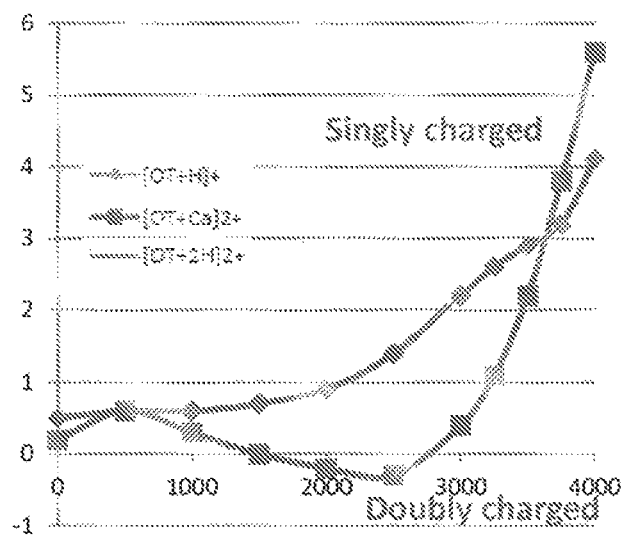
Figure 3C:
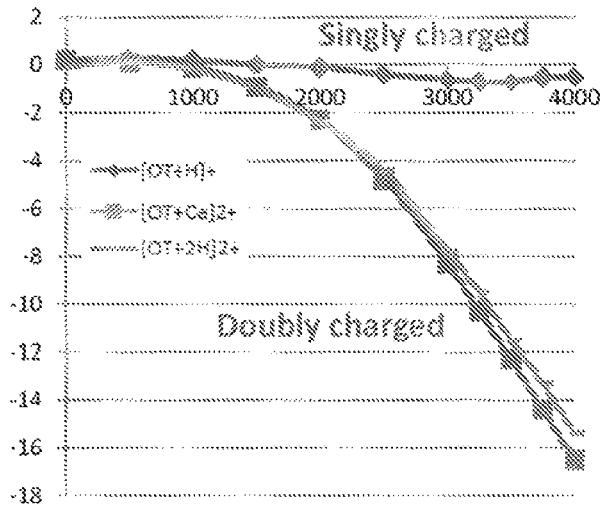
Figure 3D:
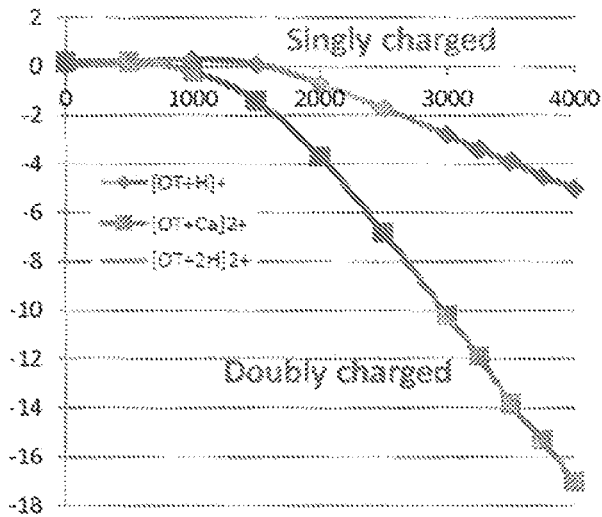

Sequence: CYIQNCPL[Ami]G
Formula: $C_{43}H_{66}N_{12}O_{12}S_2$
$[M+2H]^{2+}=504.22551$
$[M+H]^{+}=1007.44374$
$[M+Ca]^{2+}=523.19898$ Referring now to FIGS. 3A-3D, exemplary DMS SV-CoV maps of protonated or calciated oxytocin are shown with no chemical modifier (FIG. 3A), 1.5% methanol (MeOH) (FIG. 3B), 1.5% acetonitrile (AcCN) (FIG. 3C), and 1.5% isopropanol (IPA) (FIG. 3D). Each map shows singly and doubly charged protonated species, as well as doubly charged oxytocin-calcium ion complexes. Doubly charged species of oxytocin have similar behavior in DMS whether protonated ($[M+2H]^{2+}$) or complexed with calcium (i.e., calciated) ($[M+Ca]^{2+}$). As shown in FIGS. 3B and 3D, the addition of an alcohol (e.g. MeOH or IPA) as a modifier in the gas phase led to a loss of signal associated with the doubly protonated form of OT. However, a loss of signal was not associated with the calciated form of OT in the presence of the alcohol.

Conversion to a Type-B behavior of OT by addition of $Ca^{2+}$ and use of methanol improved selectivity in the detection of oxytocin. For example, operating at the SV-CoV minima of a type-B ion was demonstrated to be successful in gaining unique selectivity. $Ca^{2+}$ binds with high affinity to OT and some amount of protonated oxytocin ($[OT+2H]^{2+}$) ion was generated during ESI process if $Ca^{2+}$ was not in excess. Methanol provided a unique Type-B behavior to $[OT-Ca]^{2+}$. As shown in the following example, the present teachings also provide means to control the formation of $[OT+Ca]^{2+}$ during the LC process to take advantage of the DMS behavior with methanol.

Example 2—A Method Using Post-LC Addition of Calcium

The following conditions listed in Table 1, below, were used in the experiments described herein (see FIG. 4).

TABLE 1

| Experimental Conditions | |
|---|---|
| LC Conditions | Post-LC Additive |
| Perkin Elmer Series 200 microLC Pumps @ 400 (μL/min Kinetex C18 (2 × 100 mm) 2.7 μm | Delivered with Agilent 1100 series pump Introduced 1 mM solution of $CaCO_3$ or $CaCl_2$ at adjusted flow rate to give final concentration ranging between 25 μM to 350 μM |
| 10 minute gradient to 50% Solvent B | Approach taken to minimize system (mainly LC) contamination |
| Source Conditions | Peptide Mixture |
| TurboV Ion source @ 550° C. with Gas 1 = 30 and Gas 2 = 70 Generic source conditions All data acquired on research prototype hybrid-quadrupole time-of flight | Oxytocin, Arg-Vasopressin and 10 others all 1 pmol/μL |

A differential mobility spectrometer (SelexION™, SCIEX, Concord, ON) system (Anal. Chem. 2012, 84, 7857-7864) was mounted on a 5500 QTRAP® system (SCIEX), between a TurboV™ ESI source and the mass spectrometer's sampling orifice. The ESI probe was maintained at a voltage of 5500 V, with a source temperature of 550° C., nebulizing gas pressure of 30 psi, and auxiliary gas pressure of 70 psi. The DMS temperature was maintained at 150° C., and nitrogen was used as the curtain gas (20 psi), throttle gas (variable), and target gas (~3 mTorr) for these experiments.

As discussed above, differential mobility spectrometers for use in accord with teachings herein can have a variety of configurations, but are generally configured to resolve ions based on their mobility through a fixed or variable electric field. As will be appreciated by a person skilled in the art in light of the teachings herein, the various parameters used in the DMS can be altered, for example, in light of the isomers to be analyzed.

Figure 5A:
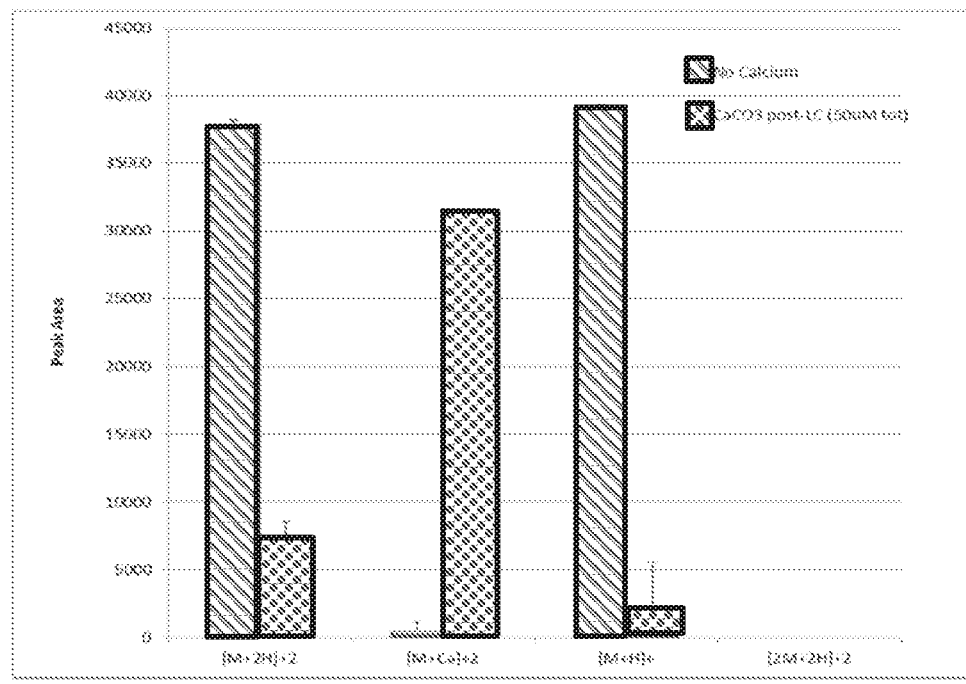
FIG. 5A depicts exemplary data for the relative amounts of various forms of an ionized peptide (oxytocin) separated using a differential mobility spectrometer with and without calcium added post-LC in accordance with aspects of various embodiments of the applicant's teachings.
Figure 5B:
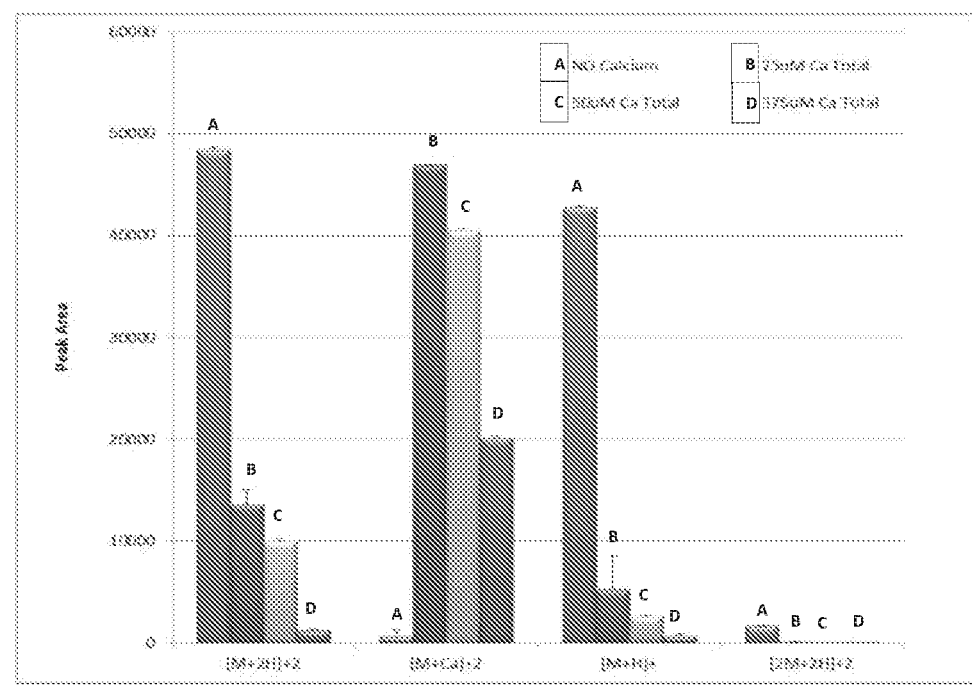
FIG. 5B depicts exemplary data for the relative amounts of various forms of an ionized peptide using a differential mobility spectrometer with various concentrations of calcium added post-LC in accordance with aspects of various embodiments of the applicant's teachings.

Referring now to FIGS. 5A and 5B, there was a significant conversion of $[M+2H]^{2+}$ ion to $[M+Ca]^{2+}$ ion in the presence of calcium compared to no calcium being added post-LC. However, a residual amount of protonated species remained even in the presence of calcium. Also, if the response of $[M+2H]^{2+}$ and $[M+H]^{30}$ is representative of OT amount, then there was about 50% loss of signal when $CaCO_3$ (50 μM) was added post-LC. A rapid titration was performed (three replicate injection) using three different flow rates of post-LC $CaCO_3$. However, increasing the total amount of $CaCO_3$ did not convert all of the oxytocin into the $[OT+Ca]^{2+}$ signal. Also, increasing the amount of $Ca^{2+}$ into the stream led to a reduction in overall signal (e.g., possibly due to suppression), as shown in FIG. 5B.

Figure 6A:
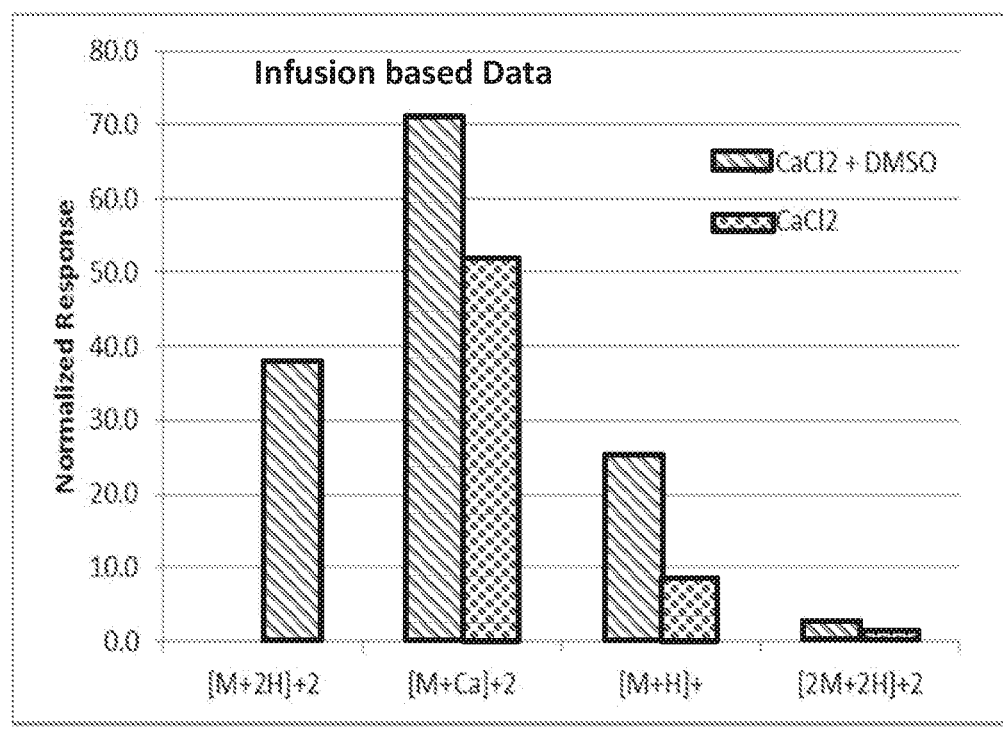
FIG. 6A depicts exemplary data for the relative amounts of various forms of an ionized peptide using a differential mobility spectrometer with the infusion of a calcium salt ($CaCl_2$) alone or with the $CaCl_2$ and DMSO.
Figure 6B:
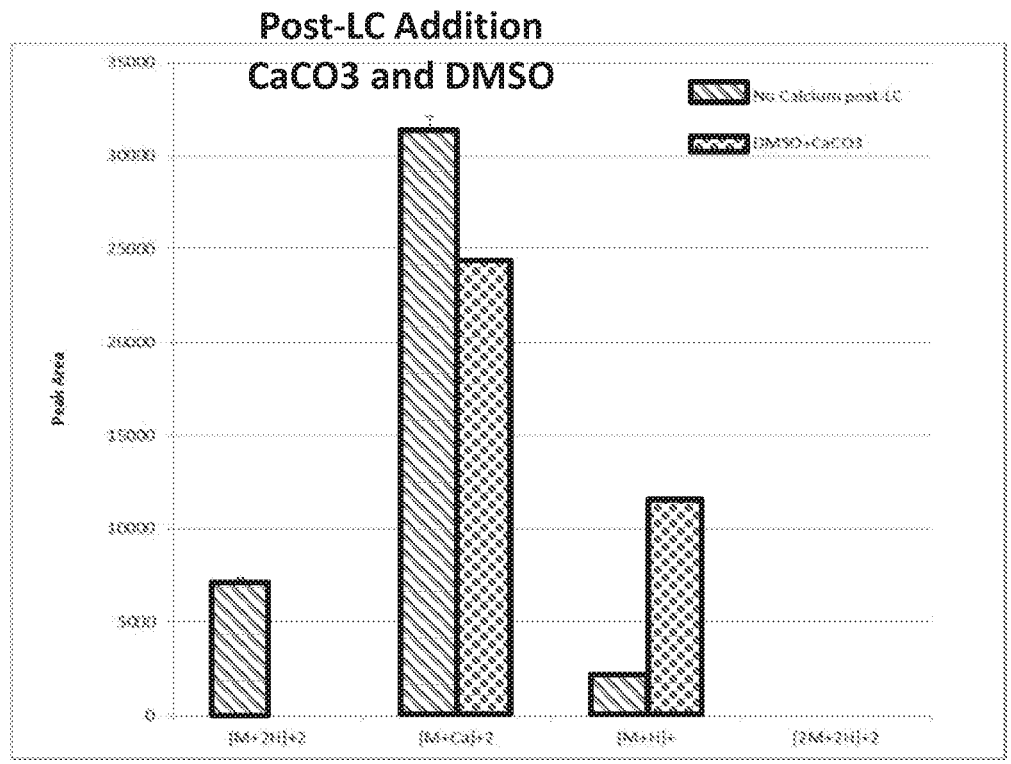
FIG. 6B depicts exemplary data for the relative amounts of various forms of an ionized peptide using a differential mobility spectrometer, with post-LC addition of calcium salt ($CaCl_2$ or $CaCO_3$) alone or with DMSO in accordance with aspects of various embodiments of the applicant's teachings.

However, referring now to FIGS. 6A and 6B, the addition of DMSO with a calcium salt eliminated all residual $[M+2H]^{2+}$ signal, while generating an increase of both the $[M+Ca]^{2+}$ and $[M+H]^{+}$ ion (FIG. 6A). This approach yielded ~89% of no additive signal (FIG. 6A). If DMSO (4% total volume) was added post-LC along with $CaCO_3$ (50 μM total), then a complete elimination of the $[M+2H]^{2+}$ ion signal was observed, with minimal loss in overall signal (FIG. 6B). There was also an increase in the [M+H]+ signal, but this could have been due to a sub-optimal DMSO concentration or use of generic source conditions.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method for separating one or more peptides in a sample, comprising:
   a. combining the sample comprising one or more peptides with a metal cation so as to form one or more peptide metal complexes;
   b. ionizing said one or more peptide metal complexes so as to form one or more peptide metal ion complexes; and
   c. transporting said one or more peptide metal ion complexes through a differential mobility spectrometer to effect separation of said one or more peptide metal ion complexes.

2. The method of claim 1, wherein the metal cation is obtained from one of an alkali metal, an alkaline earth metal, a transition metal, and salts thereof.

3. The method of claim 1, wherein the metal cation comprises calcium.

4. The method of claim 3, wherein the calcium is obtained from a calcium salt.

5. The method of claim 4, wherein the calcium salt comprises calcium chloride ($CaCl_2$) or calcium carbonate ($CaCO_3$).

6. The method of claim 1, further comprising combining the sample with dimethyl sulfoxide (DMSO).

7. The method of claim 1, wherein the one or more peptides are selected from the group consisting of polypeptides, oligopeptides, proteins, neuropeptides, lipopeptides, cyclic peptides, and lasso peptides, and peptide hormones.

8. The method of claim 1, wherein the one or more peptides are selected from the group consisting of tachykinin peptides, vasoactive intestinal peptides, pancreatic polypeptide-related peptides, opioid peptides, and calcitonin peptides.

9. The method of claim 1, wherein the one or more peptides comprises oxytocin.

10. The method of claim 1, wherein each of the one or more peptides comprises at least two amino acids.

11. The method of claim 1, further comprising adding a chemical modifier to said one or more peptide metal ion complexes in said transporting step.

12. The method of claim 11, wherein the chemical modifier is selected from the group consisting of methanol, isopropanol, acetonitrile, and dimethyl sulfoxide (DMSO).

13. The method of claim 1, further comprising detecting and/or determining the abundance of the one or more peptides in the sample.

14. The method of claim 1, further comprising modulating a throttle gas flow rate to modulate a drift time of the one or more peptide metal ion complexes in the differential mobility spectrometer.

15. The method of claim 1, wherein the sample is not passed through a liquid chromatography column prior to being transmitted through the differential mobility spectrometer.

16. The method of claim 1, wherein the differential mobility spectrometer comprises High-Field Asymmetric Waveform Ion Mobility Spectrometry (FAIMS).

17. The method of claim 1 wherein the combining the sample comprising one or more peptides with a metal cation takes place in solution.

18. A method for quantifying one or more peptides comprising:
   a. ionizing a sample containing one or more peptide metal complexes so as to form one more peptide metal ion complexes;
   b. transporting the one or more peptide metal ion complexes through a differential mobility spectrometer to effect separation of said one or more peptide metal ion complexes; and
   c. quantifying said one or more peptides.

19. A method of separating one or more peptides in a sample comprising:
   combining the sample comprising one or more peptides with a solution comprising a calcium salt and DMSO, so as to form one or more peptide calcium complexes;
   ionizing said one or more peptide calcium complexes so as to form one or more peptide calcium ion complexes;
   transporting said mixture through a differential mobility spectrometer to effect separation of said one or more peptide calcium ion complexes.

* * * * *